United States Patent [19]

Jessel, Jr. et al.

[11] Plant 4,286

[45] Aug. 1, 1978

[54] CHRYSANTHEMUM PLANT

[75] Inventors: Walter H. Jessel, Jr., Grantsville, W. Va.; William E. Duffett, Salinas, Calif.

[73] Assignee: Yoder Brothers, Inc., Barberton, Ohio

[21] Appl. No.: 739,127

[22] Filed: Nov. 5, 1976

[51] Int. Cl.[2] ..... A01H 5/00

[52] U.S. Cl. ..... Plt./74

[58] Field of Search ..... Plt./74

*Primary Examiner*—Robert E. Bagwill

*Attorney, Agent, or Firm*—Donald D. Jeffery

[57] ABSTRACT

A chrysanthemum cultivar characterized by its daisy inflorescence type and lavender pink inflorescence color, nine week flowering response, and stem strength and flower production necessary for use of the new cultivar for cut spray purposes.

3 Drawing Figures

The present invention comprises a new and distinct cultivar of *Chrysanthemum morifolium,* Ramat., hereinafter referred to by the cultivar name Camino Pink (#70309024).

Camino Pink is a product of a planned breeding program which had the objective of creating new cultivars for use as a cut spray with daisy inflorescence type, with lavender pink inflorescence color, with 9 week flowering response, and with sufficient stem strength and flower production to produce commercially acceptable quality during periods of low light periods. Such traits in combination were not present in previously available commercial cultivars.

Camino Pink was originated from a cross made in a controlled breeding program in Barberton, Ohio in 1969. The seed parent was Dramatic (#67079001; U.S. Plant Pat. No. 3,189), a bronze daisy originated by the present inventors from a cross between Dazzler (#65093001; unpatented; commercially available) and #65013002 (unnamed seedling). The pollen parent was Divinity (#57452002; unpatented; commercially available), a white anenome originated by the present inventors from a cross between #54561048 (unnamed seedling) and #541256-17 (unnamed seedling). Dazzler, #65013002, #54561048, and #541256-17 were all products of the breeding program of the present inventors.

Camino Pink was discovered and selected as a flowering plant within the progeny of the stated cross by Walter H. Jessel, Jr. and William E. Duffett on Jan. 2, 1971 in a controlled environment in Barberton, Ohio.

The first act of asexual reproduction of Camino Pink accomplished when vegetative cuttings were taken from the initial selection in February, 1971 in a controlled environment in Barberton, Ohio by a technician working under formulations established and supervised by Walter H. Jessel, Jr. and William E. Duffett. Horticultural examination of selected units initiated Feb. 28, 1972 has demonstrated that the combination of characteristics as herein disclosed for Camino Pink are firmly fixed and are retained through successive generations of asexual reproduction.

Camino Pink has not been observed under all possible environmental conditions. The phenotype may vary significantly with variations in environment such as temperature, light intensity, and daylength. The following observations, measurements, and comparisons describe plants grown in Barberton, Ohio under greenhouse conditions which approximate those generally used in commercial practice, as described in Chart A which appears at the end of the present specification. A light intensity chart of general use is shown in ASHAE Trans., Vol. 64, pg. 64, and reference is made thereto.

The following traits have been repeatedly observed and are determined to be basic characteristics of Camino Pink which in combination distinguish this chrysanthemum as a new and distinct cultivar:

1. Flat inflorescence form.
2. Daisy inflorescence type.
3. Lavender pink ray floret color with minimal color oxidation.
4. Uniform 9 week flowering response to photoperiodic short-day control.
5. Medium plant height (requires 3–4 long day weeks as a single stem plant prior to short days to attain a total height as a flowering plant of 72 to 82 cm. during the period from October through May).
6. Diameter across face of inflorescence from 60 to 80 mm. at maturity.
7. Semi-upright branching pattern.
8. High percentage grade-out in top grades (Society of American Florists standards).

The accompanying photographic drawings show typical inflorescence and foliage characteristics of Camino pink. Sheet 1 is a color photograph showing an enlarged, top plan view of the inflorescence form and type, and the ray and disc floret colors of Camino Pink. Sheet 2 is a black and white photograph showing three views of the inflorescence of Camino Pink. Sheet 3 is a black and white photograph of the foliage of Camino Pink at three stages of growth.

Of the many commercial cultivars known to the present inventors, the most similar cultivars in comparison to Camino Pink are Blue Marble (#54318A08; unpatented) and the paternal cultivar Divinity. Reference is made to attached Chart B which compares certain characteristics of Camino Pink, Blue Marble, and Divinity. General comparisons are as follow:

1. In comparison to Blue Marble, Camino Pink has longer ray floret color retention, smaller diameter across face of inflorescence, and more abundant pollen production. The ray floret color, inflorescence form, inflorescence type, plant height, and flowering response period of Camino Pink are similar to those same characteristics of Blue Marble.

2. In comparison to Divinity, Camino Pink has different ray floret color, different inflorescence type, shorter plant height, shorter flowering response period, smaller diameter across face of inflorescence, and more abundant pollen production. The inflorescence form of Camino Pink is similar to that of Divinity.

In the following description, color references are made to The Munsell Limit Color Cascade, 1972 edition. The color values were determined between 8:30 and 9:00 A.M. on May 5, 1976 under 150 foot-candle light intensity at Barberton, Ohio.

Botanical classification: *Chrysanthemum morifolium,* Ramat. cv Camino Pink.

D. Reproductive organs:

*Androecium.*—Present disc florets; moderate pollen.

*Gynoecium.*—Present both ray and disc florets.

II. PLANT

A. General appearance: Semi-upright branching pattern; medium height.

B. Foliage (see Sheets 1 and 3):

*Color (abaxial).*—19-15 to 21-15.

*Color (adaxial).*—21-15 to 21-14.

CHART A

AVERAGE GREENHOUSE CHRYSANTHEMUM ENVIRONMENTS USED FOR BARBERTON, OHIO

| SEASON | TEMPERATURES USED Night | Bright Day | Cloudy Day | LIGHTING USED | BLACK CLOTH USED | SUPP $CO_2$ |
|---|---|---|---|---|---|---|
| FALL | 65° F to 56° F | 65° F to 80° F | 60° F to 75° F | 2 to 4 weeks at 3 Hours Per Night of 7–10 f.c. | To Sept. 15 on - 5:30 PM Off-7:30 AM | From Oct. 15 300 ppm |
| WINTER | 58° F to 62° F | 65° F to 70° F | 60° F to 65° F | 2 to 5 weeks at 5 hours Per Night of 7–10 f.c. | NONE | 300 ppm |
| SPRING | 58° F to 65° F | 65° F to 80° F | 60° F to 75° F | 2 to 4 weeks at 5 Hours Per Night of 7–10 f.c. | From Mar. 15 on - 5:30 PM Off-7:30 AM | To Apr. 15 300 ppm |
| SUMMER | 62° F to 68° F | 70° F to 90° F | 65° F to 75° F | 1 to 2 weeks at 3 Hours Per Night of 7–10 f.c. | on-6:00 PM Off-8:00 AM | NONE |

CHART B

COMPARISON OF CAMINO PINK, BLUE MARBLE, AND DIVINITY

| CULTIVAR | RAY FLORET COLOR | RAY FLORET COLOR RETENTION | INFLORESCENCE FORM AND TYPE | PLANT HEIGHT | FLOWER RESPONSE | DIAMETER ACROSS FACE OF INFLORESCENCE | POLLEN PRODUCTION |
|---|---|---|---|---|---|---|---|
| Camino Pink | Lavender Pink | Good | Flat daisy | Medium | 9 week | 60 to 80 mm. | Moderate |
| Blue Marble | Lavender Pink | Poor | Flat daisy | Medium | 9 week | 60 to 85 mm. | Minimal |
| Divinity | White | Not applicable | Flat anenome | Tall | 10 week | 80 to 90 mm. | Minimal |

COMPARISONS MADE OF PLANTS GROWN IN BARBERTON, OHIO UNDER GREENHOUSE CONDITIONS AS DESCRIBED IN CHART A.

I. INFLORESCENCE (see Sheets 1 and 2)

A. Capitulum:

*Form.*—Flat.

*Type.*—Daisy.

*Diameter across face.*—60 to 80 mm.

B. Corolla of ray florets:

*Color (abaxial).*—46-6 to 46-3.

*Color (adaxial).*—46-5 streaked over 46-2.

C. Corolla of disc florets:

*Color (immature).*—24-16 to 24-11.

*Color (mature).*—24-12 to 26-9.

We claim:

1. A new and distinct cultivar of *Chrysanthemum morifolium* plant known by the cultivar name Camino Pink and particularly characterized as to uniqueness by the combined characteristics of flat inflorescence form, daisy inflorescence type, lavender pink ray floret color with minimal color oxidation, uniform nine week flowering response, medium plant height, diameter across face of inflorescence up to 80 mm. at maturity, semi-upright branching pattern, and high percentage grade-out in top SAF grades.

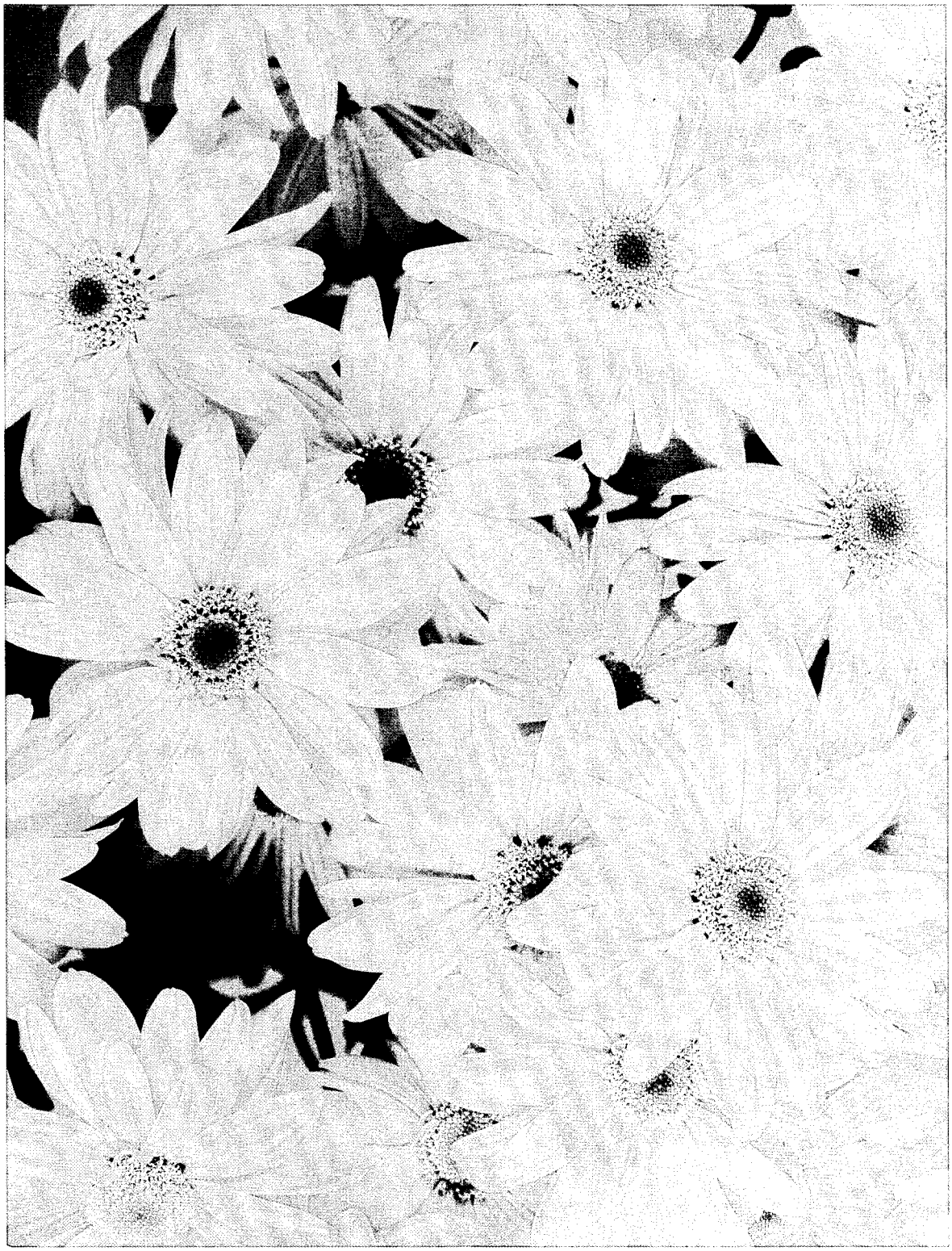

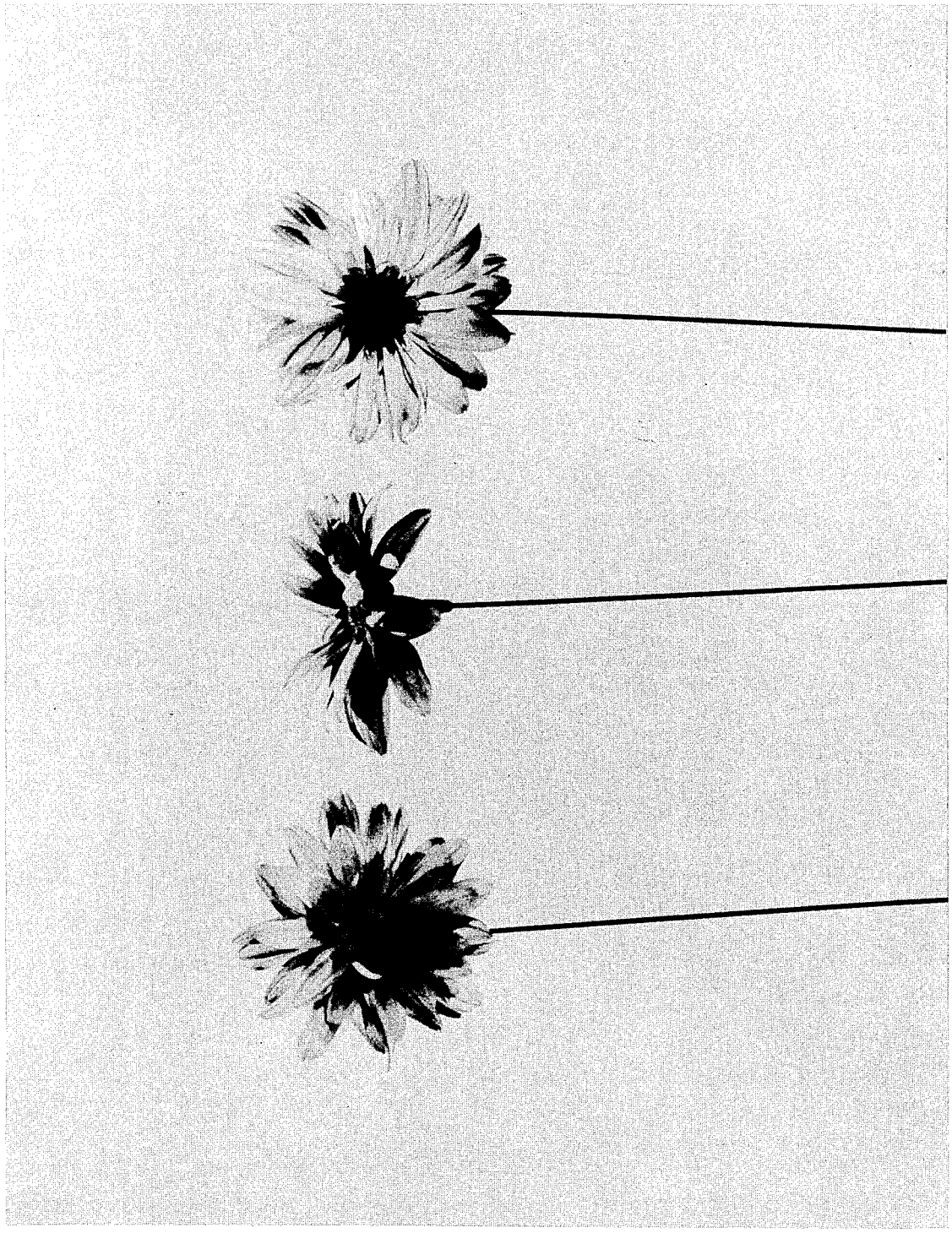

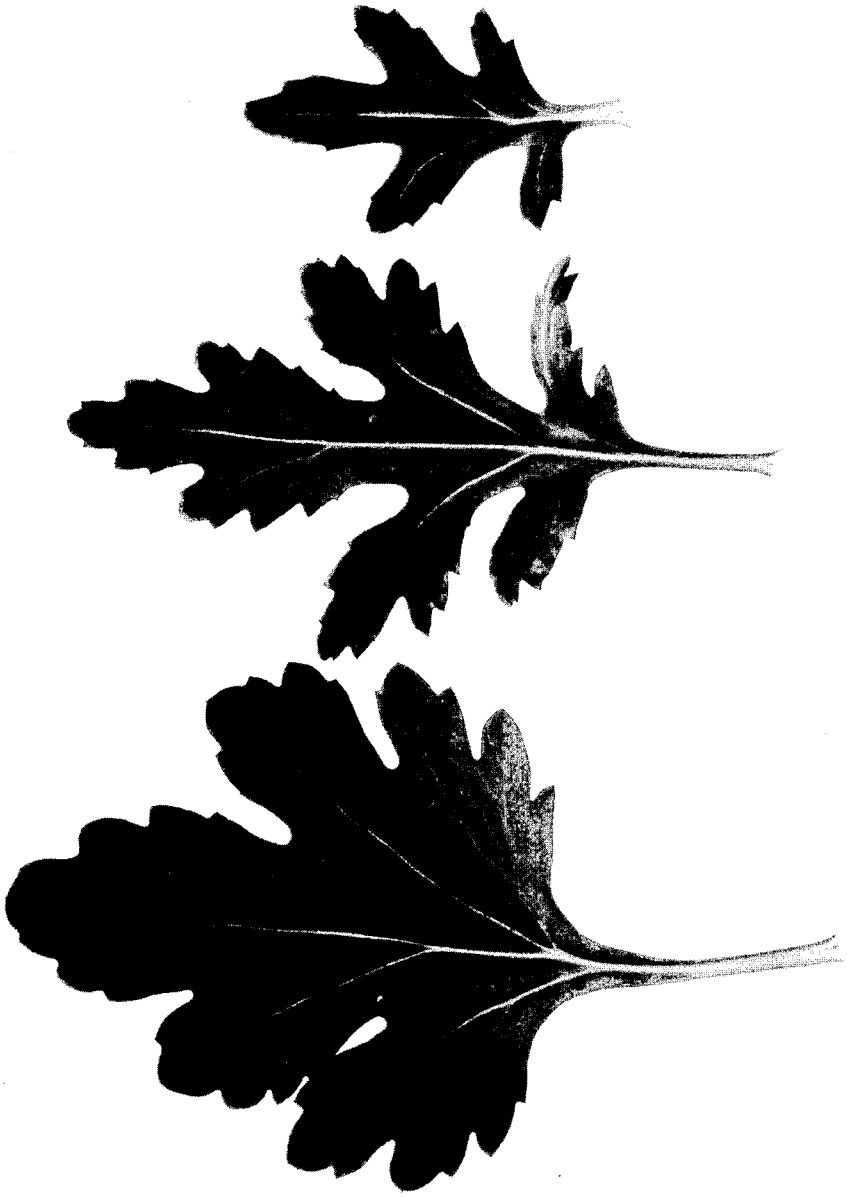

* * * * *